United States Patent
Lolis et al.

(10) Patent No.: US 12,414,927 B2
(45) Date of Patent: Sep. 16, 2025

(54) CXCR5 ANTAGONISTS AND METHODS OF TREATING DISEASES OR DISORDERS USING SAME

(71) Applicant: YALE UNIVERSITY, New Haven, CT (US)

(72) Inventors: Elias Lolis, Westport, CT (US); Francine Foss, Hamden, CT (US); Demetrios Braddock, Guilford, CT (US); Yulia Surovtseva, Branford, CT (US); Christopher Fanger, Bolton, MA (US); Mark Plummer, Westbrook, CT (US); Denton Hoyer, West Haven, CT (US); Elizabeth Spencer, Southbury, CT (US)

(73) Assignee: Yale University, New Haven, CT (US)

( * ) Notice: Subject to any disclaimer, the term of this patent is extended or adjusted under 35 U.S.C. 154(b) by 539 days.

(21) Appl. No.: 17/916,439

(22) PCT Filed: Mar. 30, 2021

(86) PCT No.: PCT/US2021/024918
§ 371 (c)(1),
(2) Date: Sep. 30, 2022

(87) PCT Pub. No.: WO2021/202553
PCT Pub. Date: Oct. 7, 2021

(65) Prior Publication Data
US 2023/0146903 A1     May 11, 2023

Related U.S. Application Data

(60) Provisional application No. 63/003,005, filed on Mar. 31, 2020.

(51) Int. Cl.
*A61K 31/196* (2006.01)
*A61K 45/06* (2006.01)
*A61P 35/04* (2006.01)

(52) U.S. Cl.
CPC ............ *A61K 31/196* (2013.01); *A61K 45/06* (2013.01); *A61P 35/04* (2018.01)

(58) Field of Classification Search
CPC ........ A61K 31/196; A61K 45/06; A61P 35/04
See application file for complete search history.

(56) References Cited

U.S. PATENT DOCUMENTS

2010/0113462 A1   5/2010   Caulfield et al.
2012/0128688 A1   5/2012   Lillard et al.

OTHER PUBLICATIONS

Hu, Shimin, et al., "Follicular T-cell lymphoma: a member of an emerging family of follicular helper T-cell derived T-cell lymphomas", Human Pathology, vol. 43, Issue 11, Nov. 2012, 1789-1798.

*Primary Examiner* — Joseph K McKane
*Assistant Examiner* — Quincy McKoy
(74) *Attorney, Agent, or Firm* — Saul Ewing LLP; Domingos Silva; Kathryn Doyle

(57) ABSTRACT

The disclosure provides compounds, and compositions comprising such compounds, that can be used to treat CXCR5-expressing cancers, especially angioimmunoblastic T cell lymphoma (AICL) and/or cutaneous T cell lymphoma (CTCL).

15 Claims, 8 Drawing Sheets

% Human CD45 in Bone Marrow

| Unpaired t test | |
|---|---|
| P value | 0.0017 |
| P value summary | ** |
| Significantly different (P < 0.05)? | Yes |
| One- or two-tailed P value? | Two-tailed |
| t, df | t=3.882 df=14 |

% Human CD45 in Peripheral Blood

| Unpaired t test | |
|---|---|
| P value | 0.0013 |
| P value summary | ** |
| Significantly different (P < 0.05)? | Yes |
| One- or two-tailed P value? | Two-tailed |
| t, df | t=4.016 df=14 |

CXCR5 ANTAGONISTS AND METHODS OF TREATING DISEASES OR DISORDERS USING SAME

CROSS-REFERENCE TO RELATED APPLICATIONS

This application is a 35 U.S.C. § 371 national phase application from, and claims priority to, International Application No. PCT/US2021/024918, filed Mar. 30, 2021, and published under PCT Article 21 (2) in English, which claims priority under 35 U.S.C. § 119(e) to U.S. Provisional Patent Application No. 63/003,005 filed Mar. 31, 2020, the entire contents of which are incorporated herein by reference.

BACKGROUND

The C—X—C chemokine receptor type 5 (CXCR5), also known as CD185 (cluster of differentiation 185) or Burkitt lymphoma receptor 1 (BLR1), is a G protein-coupled seven-transmembrane receptor for chemokine CXCL13 (also known as BLC) and belongs to the CXC chemokine receptor family. CXCR5 is specifically expressed in Burkitt's lymphoma and lymphatic tissues, such as follicles in lymph nodes and in spleen. CXCR5 enables T cells to migrate to lymph node B cell zones—this is a key step in the production of high affinity antibodies as B cells, and T cells need to perform this step in order to activate the Ig class switch.

There is a need in the art for novel compounds and/or compositions that can be used to treat certain types of cancer, especially those expressing CXCR5. The present disclosure addresses these unmet needs.

BRIEF SUMMARY

The present disclosure provides a method of treating, ameliorating, and/or preventing a CXCR5-expressing cancer in a subject.

In certain embodiments, the method comprises administering to the subject a therapeutically effective amount of a CXCR5 inhibitor, or a salt, solvate, tautomer, enantiomer, and/or diastereoisomer thereof, as described elsewhere herein and/or as known in the art.

In certain embodiments, the method comprises administering to the subject a therapeutically effective amount of a compound of formula (I), or a salt, solvate, tautomer, enantiomer, and/or diastereoisomer thereof, as described elsewhere herein.

In certain embodiments, the method comprises administering to the subject a therapeutically effective amount of a compound selected from 2-(3-methyl-2-(2-methylprop-1-en-1-yl)benzamido)-2,3-dihydro-1H-indene-2-carboxylic acid, 2-(2-isobutyl methylbenzamido)-2,3-dihydro-1H-indene-2-carboxylic acid, or a salt, solvate, or tautomer thereof, or any mixtures thereof.

In certain embodiments, the cancer is a B-cell malignancy.

In certain embodiments, the B-cell malignancy comprises at least one of diffuse large B-cell lymphoma (DLBCL), follicular lymphoma, marginal zone B-cell lymphoma (MZL) or mucosa-associated lymphatic tissue lymphoma (MALT), chronic lymphocytic leukemia (CLL), and mantle cell lymphoma (MCL).

In certain embodiments, the follicular lymphoma comprises a peripheral T-cell lymphoma (PTCL).

In certain embodiments, the PTCL comprises T follicular helper derived lymphoma, angioimmunoblastic T cell lymphoma (AITL) and/or cutaneous T cell lymphoma (CTCL).

In certain embodiments, the CTCL comprises mycosis fungoides and/or the Sezary Syndrome.

In certain embodiments, the compound is administered as a pharmaceutical composition comprising at least one pharmaceutically acceptable carrier.

In certain embodiments, the compound is the only therapeutically effective agent administered to the subject.

In certain embodiments, the compound is the only therapeutically effective agent administered to the subject in an amount that treats, ameliorates, and/or prevents the cancer in the subject.

In certain embodiments, the blood level of the compound is about 1 µM.

In certain embodiments, the subject is a mammal.

In certain embodiments, the subject is human.

In certain embodiments, the compound is administered by an administration route selected from the group consisting of inhalational, oral, rectal, vaginal, parenteral, intracranial, topical, transdermal, pulmonary, intranasal, buccal, ophthalmic, intrathecal, and intravenous.

In certain embodiments, the subject is further administered at least one additional agent that treats, ameliorates, and/or prevents the cancer.

In certain embodiments, the compound and the at least one additional agent are co-administered.

In certain embodiments, the compound and the at least one additional agent are co-formulated.

BRIEF DESCRIPTION OF THE DRAWINGS

For the purpose of illustrating the disclosure, certain embodiments of the disclosure are depicted in the drawings. However, the disclosure is not limited to the precise arrangements and instrumentalities of the embodiments depicted in the drawings.

DETAILED DESCRIPTION

Figure 1A:
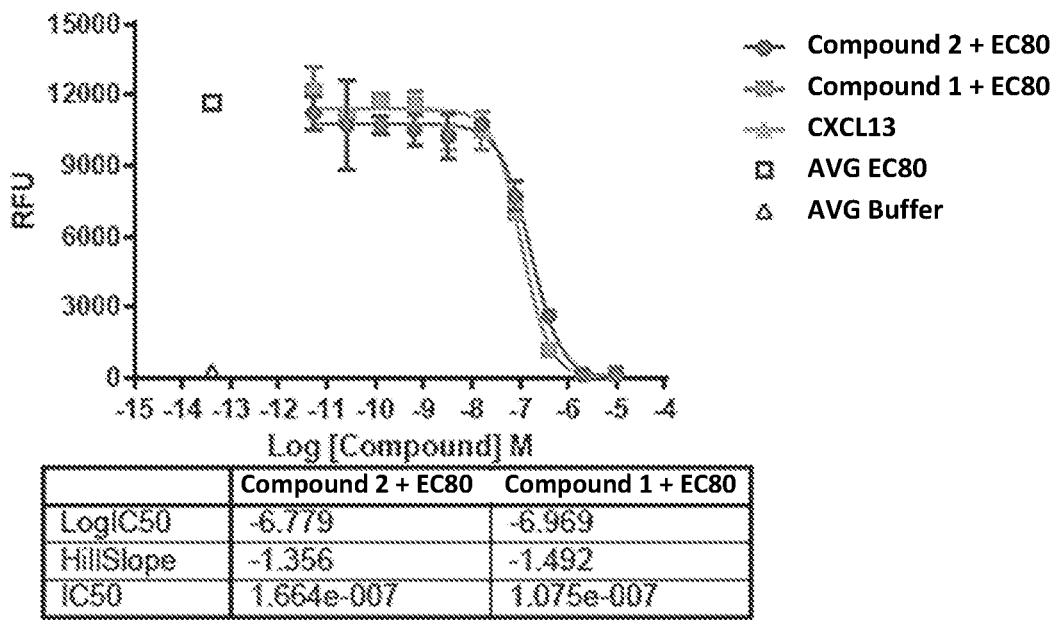
FIGS. 1A-1B illustrate inhibition of $Ga_q$-mediated $Ca^{2+}$ flux for certain compounds of the disclosure. The assays use HEK cells stably expressing functional human CXCR5 and measure inhibition of Gaq-mediated $Ca^{2+}$ flux at an $EC_{80}$ of CXCL13 agonist. Assays were performed in HBSS buffer (FIG. 1A) and HBSS buffer+1% BSA (FIG. 1B); the compounds were active in the presence of the bovine serum albumin, without significant change in an $IC_{50}$ value. Compound 1 is 2-(3-methyl-2-(2-methylprop-1-en-1-yl)benzamido)-2,3-dihydro-1H-indene-2-carboxylic acid; Compound 2 is 2-(2-isobutyl-3-methylbenzamido)-2,3-dihydro-1H-indene-2-carboxylic acid.

The disclosure relates in one aspect to certain compounds that can be used to treat cancer, especially aggressive B-cell malignancies and/or T-cell malignancies, such as but not limited to B-cell lymphomas, T-cell lymphomas, B-cell leukemias, and/or T-cell leukemias, such as but not limited to peripheral T-cell lymphoma (PTCL), such as but not limited to T follicular helper derived lymphomas, angioimmunoblastic T cell lymphoma (AITL) and/or cutaneous T cell lymphoma (CTCL) such as mycosis fungoides and the Sezary Syndrome. In certain embodiments, the compounds are CXCR5 inhibitors.

Malignancies such as AITL, follicular helper PTCL and CTCL are aggressive malignancies that arise from a dysfunctional T follicular helper (Tfh) clone. Next generation sequencing found a number of epigenetic genes that are mutated or deleted and a heterozygous mutant RhoA GTPase G17V in 50-75% of the patients, considered to be the driver of oncogenesis but only in the presence of an epigenetic gene mutation(s).

There is an unmet medical need for efficacious treatments for T-cell lymphomas, including PTCL, AITL and CTCL. About 3,000 patients/year are diagnosed with AITL in the United States, and the median survival for the disease at 2 and 5 years is about 47% and 30% survival, respectively. No therapy so far has provided survival benefit for AITL patients. Likewise, about 3,000 patients/year are diagnosed with CTCL in the United States, and the median survival for advanced stage patients, T2, T3, T4, is 12.1, 3.3, and 4.0 years respectively. The therapies available for CTCL do not provide long term quality of life or survival benefit.

As demonstrated herein, CXCR5 is a viable therapeutic target for the treatment of AITL and CTCL. CXCR5 is expressed in Tfh, Tfh-malignancies, and B-cells. It is also expressed in other cancers (breast, prostate, lung, and colon cancer) but not corresponding healthy cells. The CXCL13-CXCR5 axis is involved in proliferation/pro-survival effects and metastatic effects for T follicular helper cells and B-cells. All AITL cancer cells secrete CXCL13 and express CXCR5 receptor, and in fact the tumor microenvironment has increased secretion of CXCL13 as well. Further, CXCR5 is expressed in 50% of CTCL cases, with CXCL13 expressed in CTCL cells. Consistently, CTCL CXCR5+ patients show decreased survival (no significant survival past 4 years of diagnosis) as compared to CTCL CXCR5- patients (about 65% survival past 4 years of diagnosis). The CXCL13-CXCR5 signaling axis has never been targeted for T cell or B-cell malignancies.

As demonstrated herein, a small molecule series was shown to be potent CXCR5 inhibitors. In certain embodiments, the compounds contemplated in the disclosure are useful in treating, ameliorating, and/or preventing certain cancers, such as B-cell malignancies.

B-cell malignancies contemplated herein include, but are not limited to diffuse large B-cell lymphoma (DLBCL), follicular lymphoma, HIV associated lymphomas, EBV associated lymphomas, marginal zone B-cell lymphoma (MZL) or mucosa-associated lymphatic tissue lymphoma (MALT), small lymphocytic lymphoma (also known as chronic lymphocytic leukemia, CLL), and mantle cell lymphoma (MCL).

B-cell malignancies contemplated herein further include, but are not limited to DLBCL variants or sub-types of primary mediastinal (thymic) large B cell lymphoma, T cell/histiocyte-rich large B-cell lymphoma, primary cutaneous diffuse large B-cell lymphoma, leg type (Primary cutaneous DLBCL, leg type), EBV positive diffuse large B-cell lymphoma of the elderly, diffuse large B-cell lymphoma associated with inflammation, primary testicular diffuse large B-cell lymphoma; Burkitt's lymphoma; Lymphoplasmacytic lymphoma, which may manifest as Waldenstrom's macroglobulinemia; nodal marginal zone B cell lymphoma (NMZL); splenic marginal zone lymphoma (SMZL); intravascular large B-cell lymphoma; primary effusion lymphoma; lymphomatoid granulomatosis; primary central nervous system lymphoma; ALK-positive large B-cell lymphoma, plasmablastic lymphoma; large B-cell lymphoma arising in HHV8-associated multicentric Castleman's disease; B-cell lymphoma, unclassifiable with features intermediate between diffuse large B-cell lymphoma and Burkitt lymphoma; B-cell lymphoma, unclassifiable with features intermediate between diffuse large B-cell lymphoma and classical Hodgkin lymphoma.

In certain embodiments, the cancer is a T follicular helper derived lymphoma, such as but not limited to AITL and/or CTCL.

The teachings and contents of WO 2008/151211A1 and US20100113462 are incorporated herein in their entireties by reference. In certain embodiments, the compounds contemplated in the disclosure include a compound of formula (I), or a salt, solvate, tautomer, enantiomer, and/or diastereoisomer thereof:

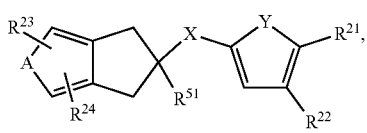
(I)

wherein:
A is CH=CH or S;
$R^{23}$ is hydrogen, halogen, $(C_1-C_4)$-alkyl, $(C_1-C_4)$-alkyloxy, $(C_1-C_4)$-alkyl-S—, or nitro;
$R^{24}$ is hydrogen or halogen when A is CH=CH, or is hydrogen, halogen, $(C_1-C_4)$-alkyl, $(C_1-C_4)$-alkyloxy, $(C_1-C_4)$-alkyl-S—, or nitro when A is S;
X is N(H)C=O, N(H)S(O)$_2$, C=ON(H), or S(O)$_2$N(H);
Y is N($R^{11}$), S, O, C($R^{12}$)=C($R^{13}$), N=C($R^{11}$), or C($R^{15}$)=N, or fused optionally substituted 5-7 membered carbocyclyl;
$R^{11}$ is hydrogen, $(C_1-C_{10})$-alkyl, hydroxy-$(C_1-C_{10})$-alkyl-, $(C_1-C_{10})$-alkyloxy, $(C_1-C_{10})$-alkyl-S(O)$_m$—, $(C_1-C_{10})$-alkylcarbonyl-, phenyl, amino, $(C_1-C_{10})$-alkylamino, or di($(C_1-C_{10})$-alkyl)amino;
$R^{12}$ is hydrogen, halogen, $(C_1-C_{10})$-alkyl, $(C_2-C_{10})$-alkenyl, $(C_3-C_6)$-cycloalkyloxy, $(C_3-C_{10})$-cycloalkenyloxy, $(C_3-C_6)$-cycloalkyl, $(C_3-C_{10})$-cycloalkenyl, $(C_3-C_6)$-cycloalkyl[$(C_1-C_4)$-alkyl or $(C_2-C_4)$-alkenyl], $(C_3-C_6)$-cycloalkyl$(C_1-C_4)$-alkyloxy, hydroxy-$(C_1-C_{10})$-alkyl-, $(C_1-C_{10})$-alkyloxy, $(C_2-C_{10})$-alkenyloxy, cyano, $(C_1-C_{10})$-alkylcarbonyl-, phenyl, or nitro;
$R^{13}$ is hydrogen, halogen, or $(C_1)$-alkyl;
$R^{14}$ is hydrogen, halogen, $(C_1-C_4)$-alkyl, hydroxy-$(C_1-C_3)$-alkyl-, $(C_1-C_3)$-alkyloxy, $(C_1-C_3)$-alkyl-S(O)$_m$—, cyano, $(C_1-C_2)$-alkylcarbonyl-, amino, $(C_1-C_3)$-alkylamino, di(($C_1-C_3)$-alkyl)amino or nitro, provided that the total number of C, N, O and S atoms which is present in $R^{14}$ does not exceed 4;
$R^{15}$ is hydrogen, halogen, $(C_1-C_{10})$-alkyl, $(C_2-C_{10})$-alkenyl, $(C_3-C_6)$-cycloalkyl, $(C_3-C_6)$-cycloalkenyl, $(C_3-C_6)$-cycloalkyl[$(C_1-C_4)$-alkyl or $(C_2-C_4)$-alkenyl], hydroxy-$(C_1-C_{10})$-alkyl-, cyano, $(C_1-C_{10})$-alkylcarbonyl-, phenyl, amino, [$(C_1-C_{10})$-alkyl or $(C_2-C_{10})$-alkenyl]amino, [$(C_1-C_{10})$-alkyl or $(C_2-C_{10})$-alkenyl](($C_1-C_{10})$-alkyl)amino or nitro;

$R^{21}$ is hydrogen when Y is C($R^{12}$)=C($R^{13}$), N=C($R^{14}$), or C($R^{15}$)=N, and is hydrogen, halogen, $(C_1-C_4)$-alkyl, hydroxy-$(C_1-C_3)$-alkyl-, $(C_1-C_3)$-alkyloxy, $(C_1-C_3)$-alkyl-S(O)$_m$—, cyano, $(C_1-C_2)$-alkylcarbonyl-, amino, $(C_1-C_3)$-alkylamino, di(($C_1-C_3)$-alkyl)amino or nitro when Y is N($R^{11}$), S, or O, provided that the total number of C, N, O and S atoms which is present in $R^{21}$ does not exceed 4;
$R^{22}$ is hydrogen, halogen, $(C_1)$-alkyl when Y is C($R^{12}$)=C($R^{13}$), N=C($R^{14}$), or C($R^{15}$)=N, or is hydrogen, hydroxy-$(C_1-C_3)$-alkyl-, $(C_1-C_3)$-alkyloxy, $(C_1-C_3)$-alkyl-S(O)$_m$—, cyano, $(C_1-C_2)$-alkylcarbonyl-, amino, $(C_1-C_3)$-alkylamino, di(($C_1-C_3)$-alkyl)amino or nitro when Y is N($R^{11}$), S, or O, provided that the total number of C, N, O and S atoms which is present in $R^{22}$ does not exceed 4;
$R^{51}$ is COOH or CONH($R^{53}$);
$R^{53}$ is $R^{55}$—SO$_2$— or tetrazolyl;
$R^{55}$ is $(C_1-C_4)$-alkyl or phenyl optionally substituted by one or more identical or different substituents chosen from the group consisting of halogen, $(C_1-C_4)$-alkyl, $(C_1-C_4)$-alkyloxy, $(C_1-C_4)$-alkyl-sulfonyl and cyano; and
m is 0, 1, or 2;
wherein all phenyl groups herein can independently of each other be optionally substituted by one or more identical or different substituents chosen from the group consisting of halogen, $(C_1-C_4)$-alkyl, $(C_1-C_4)$-alkyloxy, $(C_1-C_4)$-alkyl sulfonyl and cyano;
wherein all alkyl groups herein can independently of each other be optionally substituted by one or more fluorine atoms.

In certain embodiments, the compounds contemplated in the disclosure include at least one of the following, or a salt, solvate, tautomer, enantiomer, and/or diastereoisomer thereof:

2-(2-Allyloxy-3-methyl-benzoylamino)-indan-2-carboxylic acid,
2-(2-Isopropoxy-3-methyl-benzoylamino)-indan-2-carboxylic acid,
2-(2-Cyclobutoxy-3-methyl-benzoylamino)-indan-2-carboxylic acid,
2-(2-Cyclopropylmethoxy-3-methyl-benzoylamino)-indan-2-carboxylic acid,
2-(2-sec-Butoxy-3-methyl-benzoylamino)-indan-2-carboxylic acid,
2-(3-Chloro-2-isopropoxy-benzoylamino)-indan-2-carboxylic acid,
2-(2-Allyloxy-3-chloro-benzoylamino)-indan-2-carboxylic acid,
2-(3,5-Dichloro-2-cyclobutoxy-benzoylamino)-5-fluoro-indan-2-carboxylic acid,
2-(3,5-Dichloro-2-isopropoxy-benzenesulfonylamino)-indan-2-carboxylic acid,
2-(2-Allyloxy-3,5-dichloro-benzenesulfonylamino)-indan-2-carboxylic acid,
2-[(5,6,7,8-Tetrahydro-naphthalene-1-carbonyl)-amino]-indan-2-carboxylic acid,
1,3-Dimethyl-5-[(5,6,7,8-tetrahydro-naphthalene-1-carbonyl)-amino]-5,6-dihydro-4H-cyclopenta[c]thiophene-5-carboxylic acid,
5-Methoxy-2-[(5,6,7,8-tetrahydro-naphthalene-1-carbonyl)-amino]-indan-2-carboxylic acid,
2-[(5,6,7,8-Tetrahydro-naphthalene-1-carbonyl)-amino]-5-trifluoromethyl-indan-2-carboxylic acid,
5-Fluoro-2-[(5,6,7,8-tetrahydro-naphthalene-1-carbonyl)-amino]-indan-2-carboxylic acid, 5-(2-Isopropoxy-3-methyl-benzoylamino)-1,3-dimethyl-5,6-dihydro-4H-cyclopenta[c]thiophene-5-carboxylic acid, 2-(2-Isopropoxy-3-methyl-benzoylamino)-5-methoxy-indan-2-carboxylic acid, 2-(2-Isopropoxy-3-methyl-benzoylamino)-5-trifluoromethyl-indan-2-carboxylic acid, 5-Fluoro-2-(2-isopropoxy-3-methyl-benzoylamino)-indan-2-carboxylic acid, 2-(2-Cyclobutoxy-3-methyl-benzoylamino)-5-trifluoro-indan-2-carboxylic acid, 5-Bromo-2-(2-cyclobutoxy-3-methyl-benzoylamino)-indan-2-carboxylic acid, 2-(2-Cyclobutoxy-3-methyl-benzoylamino)-5-fluoro-indan-2-carboxylic acid, 2-(2-Cyclobutoxy-3-methyl-benzoylamino)-5,6-difluoro-indan-2-carboxylic acid, 2-[3-Methyl-2-((Z)-pent-1-enyl)-benzoylamino]-indan-2-carboxylic acid, 2-(3-Methyl-2-pentyl-benzoylamino)-indan-2-carboxylic acid, 2-[2-(1-Ethyl-but-1-enyl)-3-methyl-benzoylamino]-indan-2-carboxylic acid, 2-[2-(1-Ethyl-butyl)-3-methyl-benzoylamino]-indan-2-carboxylic acid, 2-(2-Cyclopent-1-enyl-3-methyl-benzoylamino)-indan-2-carboxylic acid, 2-(2-Cyclopentyl-3-methyl-benzoylamino)-indan-2-carboxylic acid, 2-[3-Methyl-2-(2-methyl-propenyl)-benzoylamino]-indan-2-carboxylic acid, 2-(2-Isobutyl-3-methyl-benzoylamino)-indan-2-carboxylic acid, 2-[2-(2-Cyclopropyl-vinyl)-3-methyl-benzoylamino]-indan-2-carboxylic acid, 2-[2-(2-Cyclopropyl-ethyl)-3-methyl-benzoylamino]-indan-2-carboxylic acid, 2-(2-Cyclohex-1-enyl-3-methyl-benzoylamino)-indan-2-carboxylic acid, 2-[3-Methyl-2-(1-propenyl)-benzoylamino]-indan-2-carboxylic acid, 2-(3-Methyl-2-propyl-benzoylamino)-indan-2-carboxylic acid, 2-[3-Methyl-2-((E)-pent-enyl)-benzoylamino]-indan-2-carboxylic acid, 5-Fluoro-2-[3-methyl-2-(2-methyl-propenyl)-benzoylamino]-indan-2-carboxylic acid, 5-Fluoro-2-(2-isobutyl-3-methyl-benzoylamino)-indan-2-carboxylic acid, 2-(2-Cyclopent-1-enyl-3-methyl-benzoylamino)-5-fluoro-indan-2-carboxylic acid, 5-Fluoro-2-[3-methyl-2-((E)-propenyl)-benzoylamino]-indan-2-carboxylic acid, 5-Fluoro-2-(2-isobutyl-3-methyl-benzoylamino)-indan-2-carboxylic acid, 5,6-Difluoro-2-[3-methyl-2-(2-methyl-propenyl)-benzoylamino]-indan-2-carboxylic acid, 5,6-Difluoro-2-(2-isobutyl-3-methyl-benzoylamino)-indan-2-carboxylic acid, 5,6-Difluoro-2-(3-methyl-2-propenyl-benzoylamino)-indan-2-carboxylic acid, 5,6-Difluoro-2-(3-methyl-2-propyl-benzoylamino)-indan-2-carboxylic acid, 5-Bromo-2-[3-methyl-2-((E)-propenyl)-benzoylamino]-indan-2-carboxylic acid, 2-[(2-Chloro-6-methyl-benzoyl)-amino]-indane-2-carboxylic acid, 2-[(2-Methylthiolbenzen-1-carbonyl)-amino]-indan-2-carboxylic acid, 2-(5-Chloro-2-cyclobutoxy-3-methyl-benzoylamino)-indan-2-carboxylic acid, 2-(2-Isobutyryl-3-methyl-benzoylamino)-indan-2-carboxylic acid, 2-(2,3-Dimethyl-benzoylamino)-indan-2-carboxylic acid, 2-(3-Cyano-2-methyl-benzoylamino)-indan-2-carboxylic acid, 2-[(Biphenyl-2-carbonyl)-amino]-indan-2-carboxylic acid, 2-[2-(1,1-Dimethyl-propyl)-benzoylamino]-indan-2-carboxylic acid, 2-(2-Cyclobutoxy-3-methyl-benzoylamino)-4,5-dichloro-indan-2-carboxylic acid, 2-(2-Cyclobutoxy-3-methyl-benzoylamino)-5-chloro-indan-2-carboxylic acid, 2-(2-Cyclobutoxy-3-methyl-benzoylamino)-4-fluoro-indan-2-carboxylic acid, 2-(2-Cyclobutyloxy-3-methylbenzoylamino)indan-2-acetic acid, 2-(3-Bromo-2-methylbenzoylamino)indan-2-carboxylic acid, 2-(5-Bromo-2-cyclobutoxy-3-methyl-benzoylamino)-indan-2-carboxylic acid, 2-(2-Isopropyl sulfanyl-benzoylamino)-indan-2-carboxylic acid, 2-(5-Chloro-2-cyclobutoxy-3-methyl-benzoylamino)-5-fluoro-indan-2-carboxylic acid, 2-{[2-(Ethyl-methyl-amino)-pyridine-3-carbonyl]-amino}-indan-2-carboxylic acid, 2-{[2-(Allyl-methyl-amino)-pyridine-3-carbonyl]-amino}-indan-2-carboxylic acid, 2-{[2-(Isopropyl-methyl-amino)-pyridine-3-carbonyl]-amino}-indan-2-carboxylic acid, 2-{[5-Chloro-2-(isopropyl-methyl-amino)-pyridine-3-carbonyl)-amino]-indan-2-carboxylic acid, 4,5-Difluoro-2-[3-methyl-2-(2-methyl-propenyl)-benzoylamino]-indan-2-carboxylic acid, 4,5-Difluoro-2-(2-isobutyl-3-methyl-benzoylamino)-indan-2-carboxylic acid, 4,7-Difluoro-2-[3-methyl-2-(2-methyl-propenyl)-benzoylamino]-indan-2-carboxylic acid, 4,7-Difluoro-2-(2-isobutyl-3-methyl-benzoylamino)-indan-2-carboxylic acid, 5-Chloro-2-(2-isobutyl-3-methyl-benzoylamino)-indan-2-carboxylic acid, 5-Chloro-2-[3-methyl-2-(2-methyl-propenyl)-benzoylamino]-indan-2-carboxylic acid, 2-(5,6,7,8-Tetrahydro-naphthalen-1-ylcarbamoyl)-indan-2-carboxylic acid, 2-Cyclobutoxy-N-(2-methanesulfonylaminocarbonyl-indan-2-yl)-3-methyl-benzamide, 2-Cyclobutoxy-3-methyl-N-(2-trifluoromethanesulfonylaminocarbonyl-indan-2-yl)-benzamide, 2-Cyclopent-1-enyl-3-methyl-N-(2-trifluoromethanesulfonylaminocarbonyl-indan-2-yl)-benzamide, 2-Cyclobutoxy-3-methyl-N-[2-(1H-tetrazol-5-yl)-indan-2-yl]-benzamide, and 2-[2-(2-Methyl-propenyl)-3-trifluoromethyl-benzoylamino]-indan-2-carboxylic acid.

Representatives compounds contemplated in the disclosure include, but are not limited to, Compound 1 and Compound 2, or a salt, solvate, tautomer, enantiomer, and/or diastereoisomer thereof:

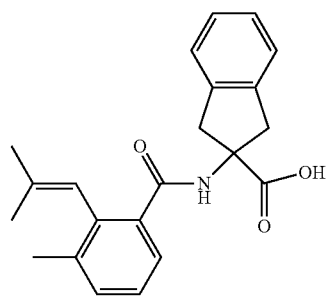 [SMILES: CC(C)=Cc1c(C)cccc1C(=O)NC1(C(=O)O)Cc2ccccc2C1]

Compound 1: 2-(3-methyl-2-(2-methylprop-1-en-1-yl)benzamido)-2,3-dihydro-1H-indene-2-carboxylic acid

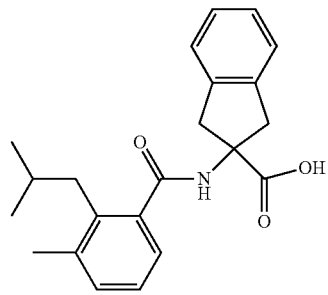 [SMILES: Cc1cccc(C(=O)NC2(C(=O)O)Cc3ccccc3C2)c1CC(C)C]

Figure 1B:
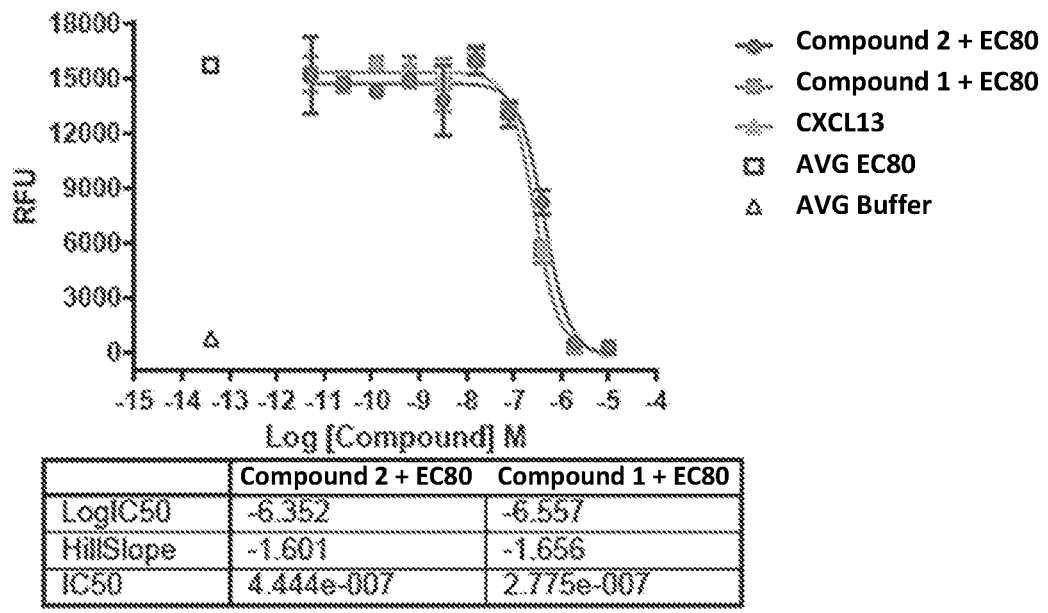
Figure 2A:
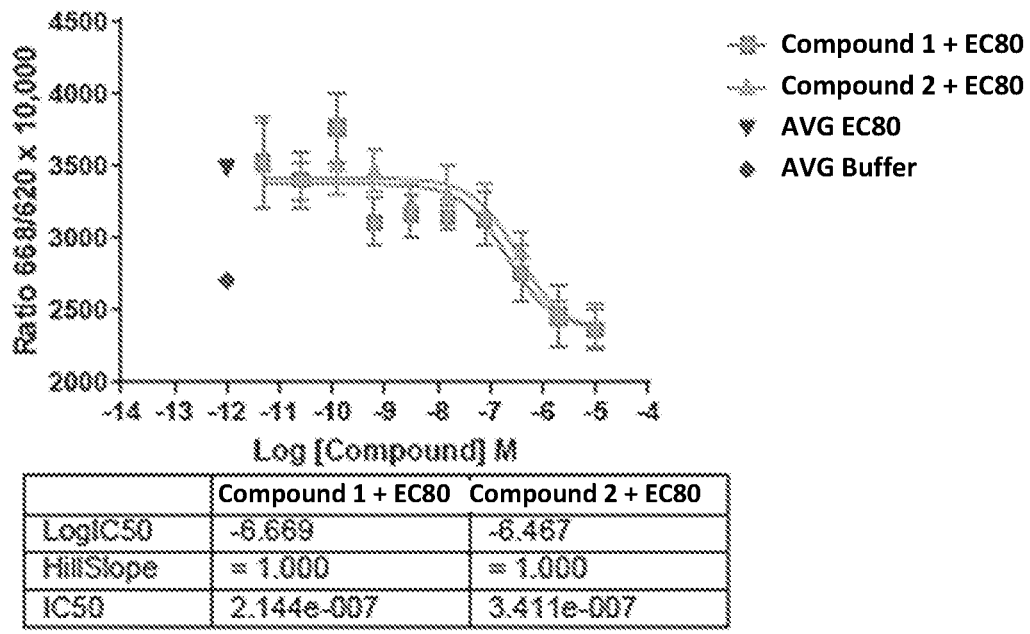
FIGS. 2A-2B illustrate inhibition of Gat-mediated decrease of cAMP for certain compounds of the disclosure. The assays use HEK cells stably expressing functional human CXCR5 and measure inhibition of Gat-mediated decrease of cAMP at an $EC_{80}$ of CXCL13. Assays were performed in HBSS buffer (FIG. 2A) and HBSS buffer+1% BSA (FIG. 2B); the compounds were active in the presence of the bovine serum albumin, without significant change in an $IC_{50}$ value.
Figure 2B:
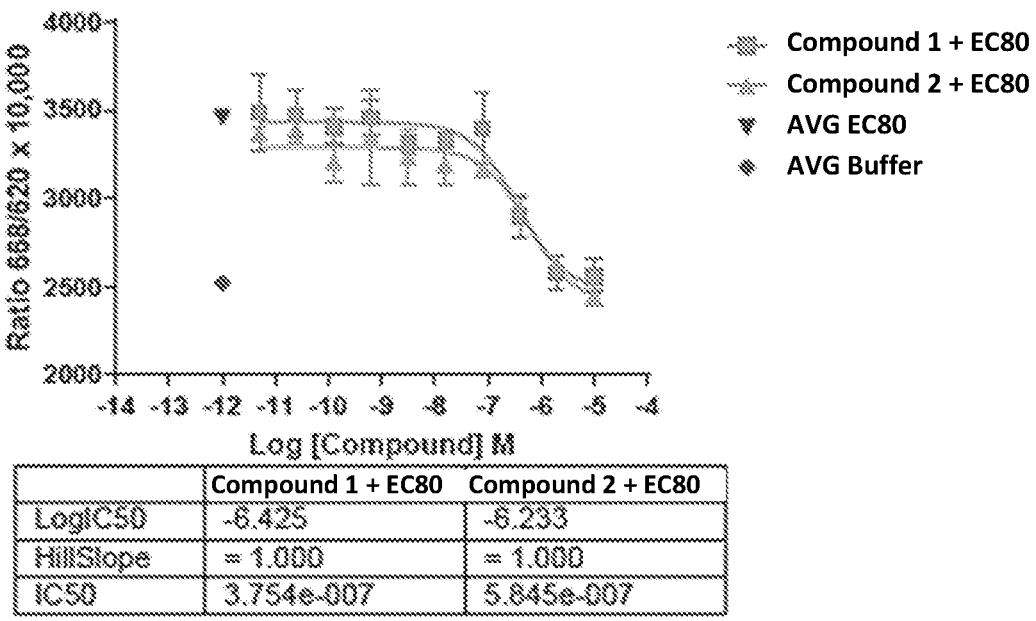

Compound 2: 2-(2-isobutyl-3-methylbenzamido)-2,3-dihydro-1H-indene-2-carboxylic acid Compound 1 and Compound 2 exhibited sub-micromolar activity in functional assays, in the presence or absence of BSA: a calcium assay (FIGS. 1A-1B; Multiscreen™ Calcium 1.0 No Wash kit; Multispan Inc., Cat #MSCA01-1) and a cyclic AMP assay (FIGS. 2A-2B; HTRF cAMP HiRange Kit; CisBio, Cat #62AM6PEC) mediated by $G\alpha_q$ and $G\alpha_{i2}$, respectively. These assays were performed in division-arrested HEK-293 cells transfected with human CXCR5. The CXCL13 ligand was used as agonist.

Figure 3:
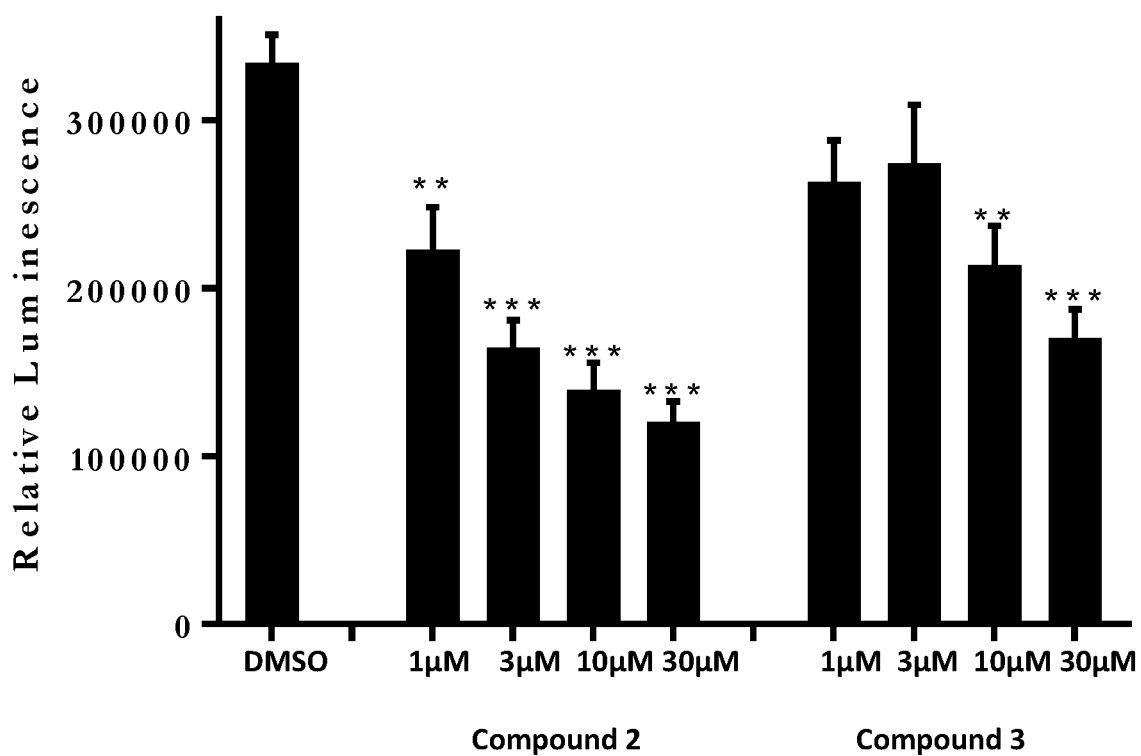
FIG. 3 illustrates proliferation of the CXCR5-expressing Burkitt's B-cell lymphoma cell line (Raji cell line) over a 7-day period in the media containing 5% FBS in the presence of various doses of Compound 2 or Compound 3 (1-(2-isobutyl-3-methylbenzamido)-2,3-dihydro-1H-indene-1-carboxylic acid). This 7-day experiment shows a dose-dependent decrease in proliferation for Compound 2. DMSO is shown as a negative control. The chemical analogue Compound 3 was less potent than Compound 2. , p,<0.01; *, p<0.005 relative to DMSO.

At this time a Tfh or AITL cell line has not been developed. Thus, a B-cell lymphoma cell line (Raji) was used to determine whether the contemplated compounds can inhibit proliferation. In this experiment, Compound 2 was compared to analogue Compound 3 over a 7-day period (FIG. 3). Compound 2 clearly inhibited proliferation in that assay, suggesting Burkitt lymphoma (and other B-cell lymphomas) can also be attractive therapeutic targets.

Figure 4:
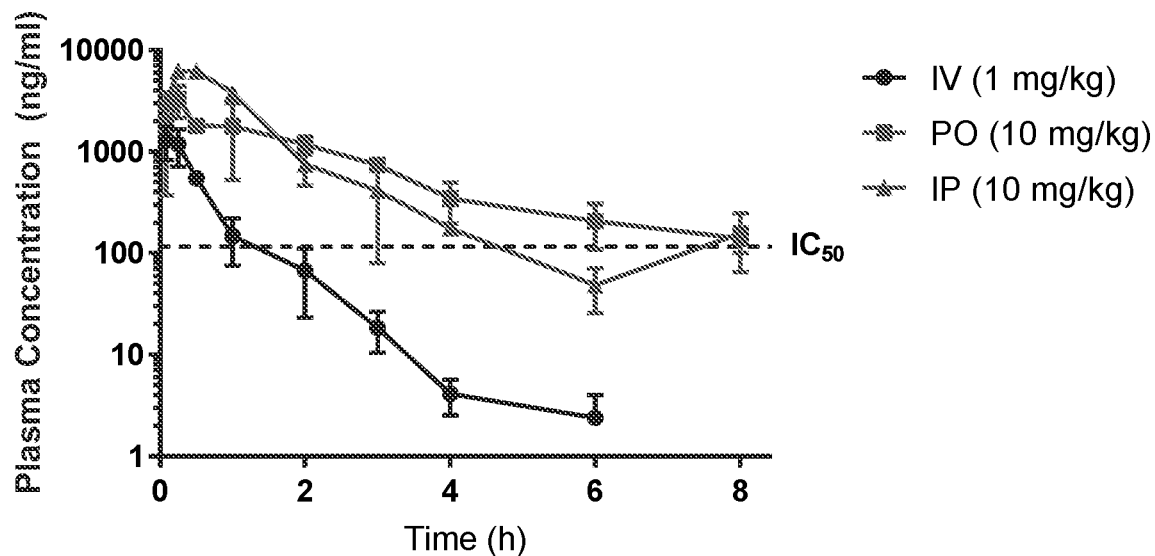
FIG. 4 illustrates in vivo PK results for a single dose of Compound 2, comprising a single administration, by three distinct routes. Three groups of 30 mice (male, CD-1) were dosed via one route per group (PO, IP, or IV). Single dose level was used per route of administration. Dosing level (mg/kg): IV (1 mg/kg); PO (10 mg/kg); and IP (10 mg/kg). Plasma samples were collected at 10 time points up to 24 hr, including 5, 15, 30, 60, 120, 180, 240, 360, 480, and 1440 minutes post dosing collection timepoints. Blood collections were terminal for each mouse, so triplicate data was obtained for each time point. Based on the clinical observations, the original IV group showed labored breathing, decreased activity, and death. The IV arm was subsequently dosed at 0.2 mg/mL delivered at 5 mL/kg, without any adverse observations.
Figure 5:
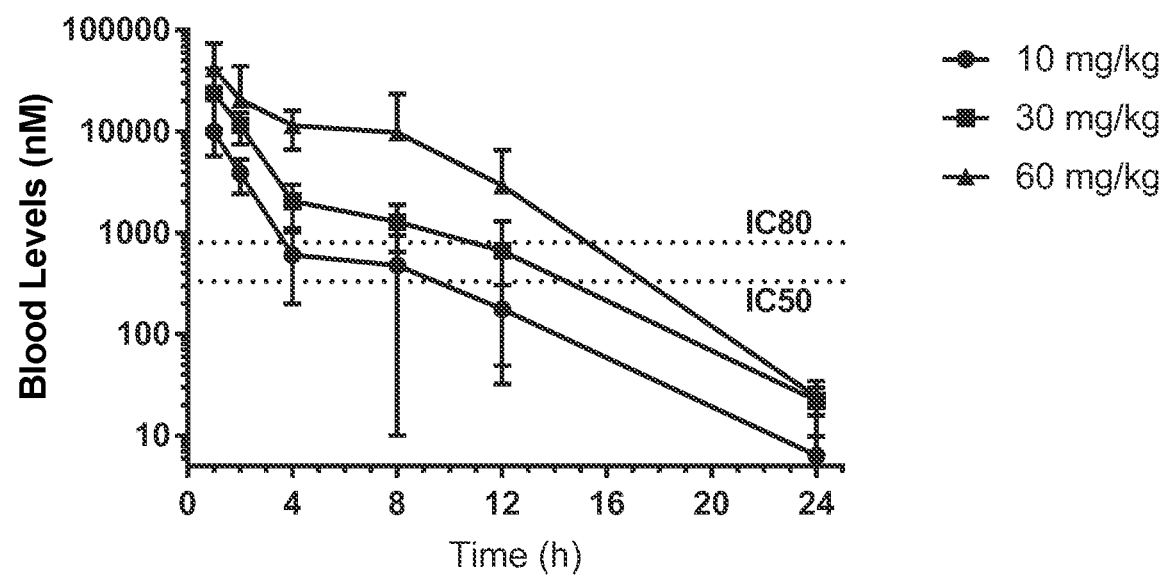
FIG. 5 illustrates in vivo PK results for multiple doses of Compound 2 administered orally. 9 female CB.17 SCID mice per group were used except for vehicle control group, where 15 mice were tested. Three drug doses were used (10, 30 and 60 mg/kg), with dosing volume of 10 mL/kg (0.200 mL/20 g mouse) for each dose. Volume was adjusted for body weight, and analysis was run at 6 different time points. There was a clear increase in compound blood level versus compound amount administered.
Figure 7A:
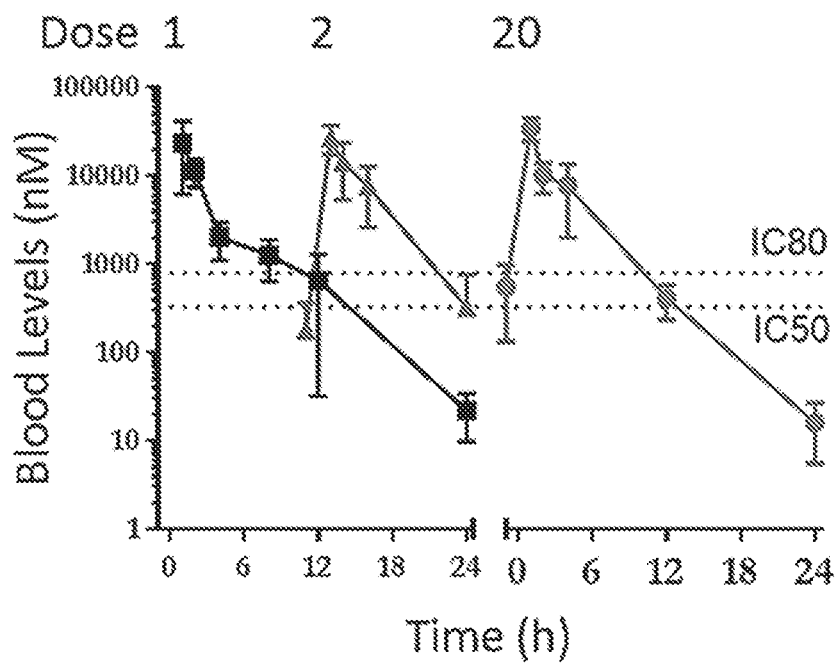
FIGS. 7A-7B illustrate in vivo PK results for multiple doses of Compound 2 (30 mg/kg) administered orally over 10 days. Pharmacokinetic study confirmed bioavailability, and 10-day study at 30 mg/kg demonstrated tolerability. Blood levels of Compound 2 overlapped for each dose over 10-day period, indicating that compound metabolism was unchanged. No change in slope of decrease indicated no change in rate of metabolism. Blood levels remained above $IC_{50}$ for full 12 hours between doses
Figure 7B:
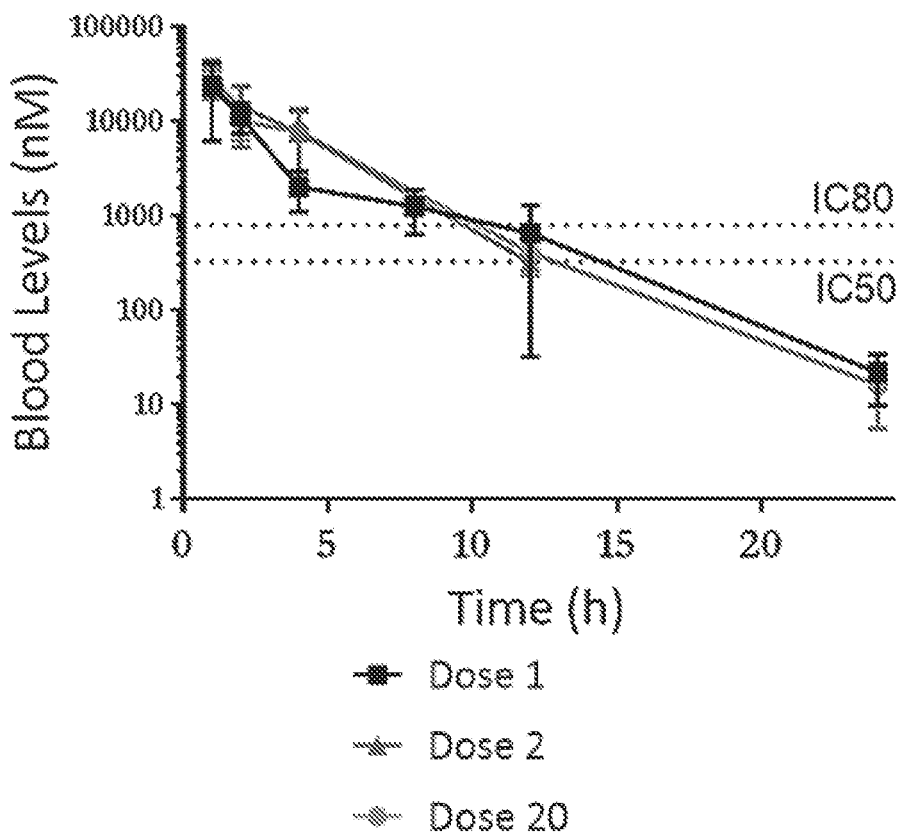

For suitability of murine AITL patient derived xenografts (PDX) studies, pharmacokinetics (PK) of Compound 2 were determined by IV, oral, and IP administration (FIG. 4). These parameters provided confidence for oral administration studies at different doses and are suitable for further PK studies at 24-hour measurement at different oral doses. The study allowed one to determine the dose that results in a blood level of $\sim IC_{80}$. Studies with 10, 30, and 60 mg/kg doses indicated blood levels of Compound 2 were slightly less than an $IC_{80}$ at dose of 30 mg/kg (FIG. 5). This result was recapitulated in a 10-day oral dosing study at 30 mg/kg every 12 hours (FIGS. 7A-7B). Superposition of the first two doses and the $20^{th}$ dose indicated that there is no change metabolism over the 10-day dosing.

Figure 6:
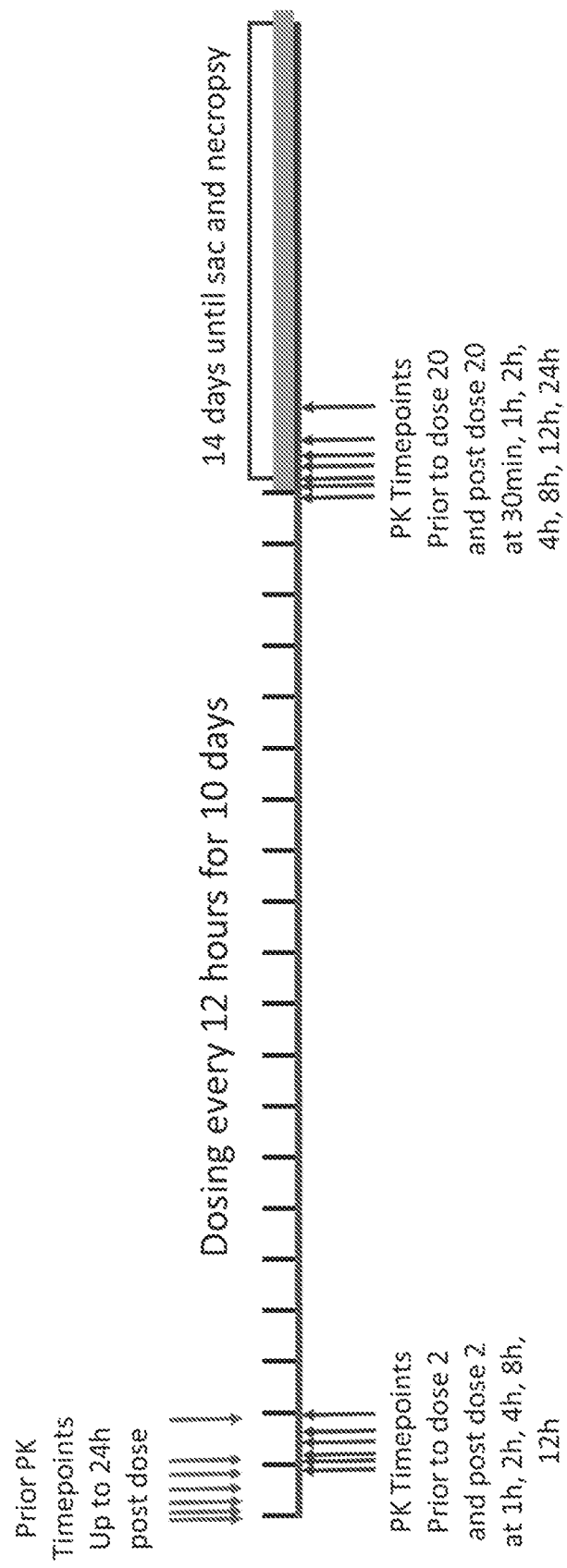
FIG. 6 illustrates a dosing scheme for oral administration of Compound 2 over 10 days. Female CB.17 SCID mice were dosed according to the table shown: Groups 1-2 were treated with the drug and Group 3 animals were treated with vehicle control. Mice were orally dosed at 30 mg/kg every 12 hours for 10 days. Group 2 (18 animals total, alternating animals) were used for PK blood analysis, and Group 1 (5 animals total) were sacrificed at end point for gross necropsy. All animals were observed to be in good health during dosing and for 2 weeks following.
Figure 8:
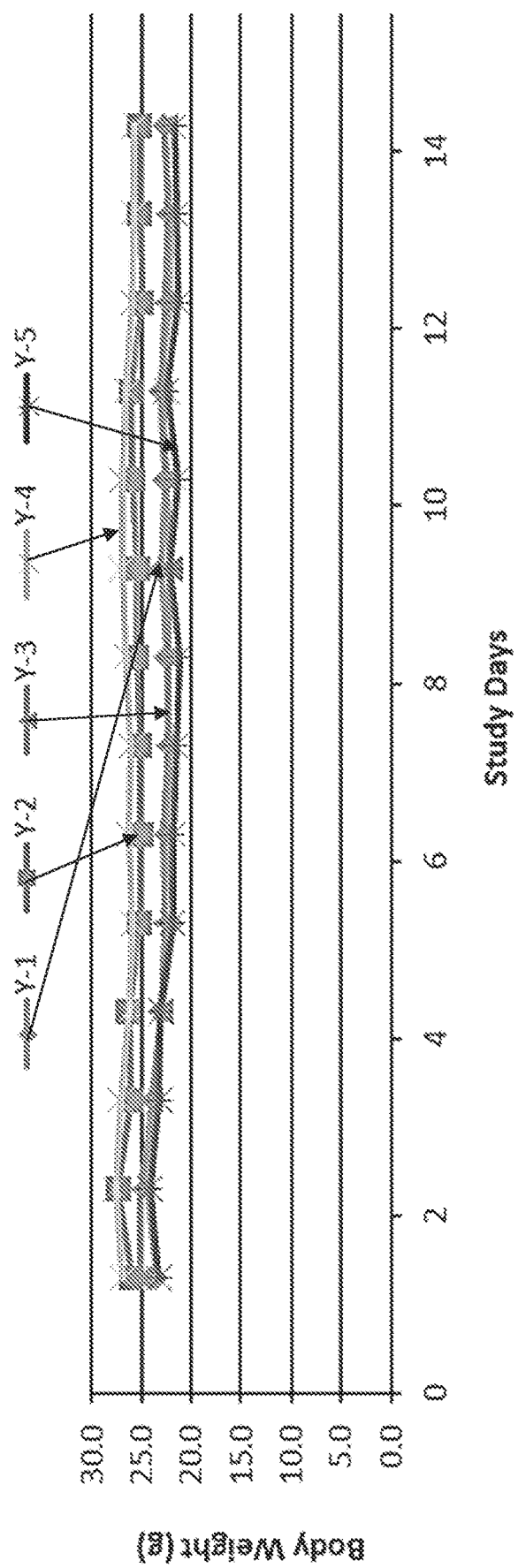
FIG. 8 illustrates absolute body weight for mice treated with Compound 2, 40 mg/kg BID. 5 NSG mice (highly immunodeficient, same strain as in the in vivo efficacy study) were tested. Compound 2 was administered via oral gavage, BID (twice a day) for 14 days. No morbidity was observed. Body weight was monitored daily. Mean body weight loss was <4%, confirming tolerability.

It was decided that a dose of 40 mg/kg would be used in the AITL PDX studies (design outlined in FIG. 6). Prior to the study, preliminary 1-week toxicity studies were performed on the NSG immunocompromised mice (NOD/SCID, IL-2R knockout) that would be used on the AITL PDX study (FIG. 8). At 40 mg/ml of Compound 2, the mice did not gain weight as fast as the mice treated with vehicle. There were no other abnormalities observed during this study.

Figure 9A:
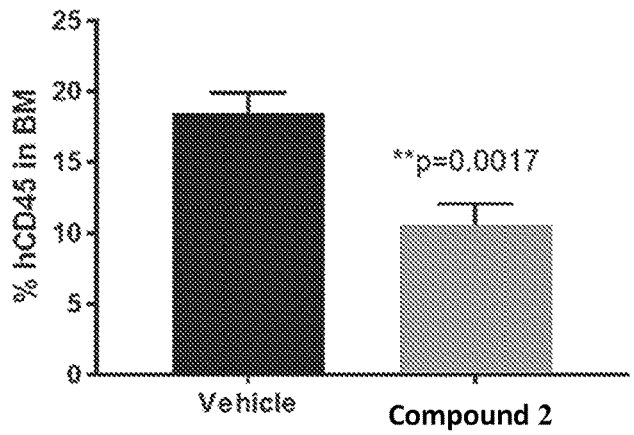
FIGS. 9A-9B illustrate CD45 levels in bone marrow (FIG. 9A) and peripheral blood (FIG. 9B) of mice treated with Compound 2 or vehicle. 8 NSG (NOD/SCID, IL-2R knockout) mice (8 animals per group) were implanted with patient-derived AITL tissue. Compound 2 binds to human but not to murine CXCR5. Animals were treated with vehicle or 40 mg/kg Compound 2 via oral gavage 2×/day. t test comparing all mice at the time of sacrifice was performed to analyze the data. Error bars—SEM. Significantly reduced tumor loads in both peripheral blood and bone marrow were observed in drug-treated group compared to vehicle control.
Figure 9B:
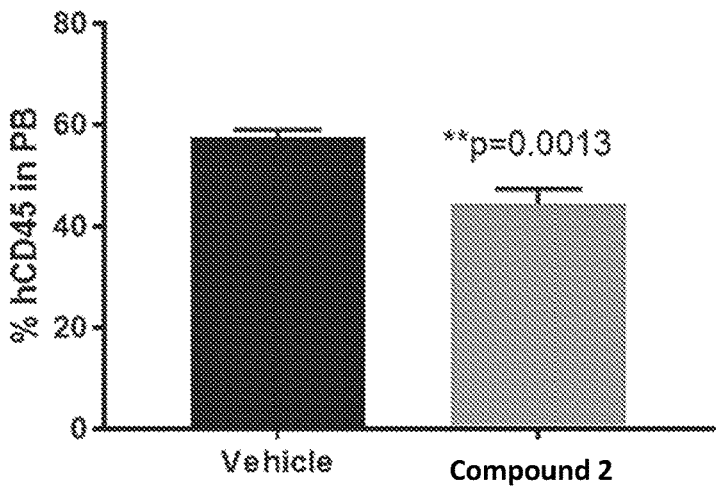

For in vivo efficacy study, mice were implanted with AITL PDX and engraftment levels were quantified in each animal as circulating human CD45+ cells levels in blood. Dosing began when average engraftment reached 0.13%, and the cohort was treated for 42 days. The mice were monitored weekly for weight loss and daily for any clinical mortality observation. Only 1 treated mouse lost weight (14%) during the first week but gained it back and was otherwise stable similar to the other mice. Blood was drawn at 0, 14, and 28 days after the dosing started, and before euthanasia to measure tumor burden. All mice lived to 35 days when, over the following week, mice that displayed considerable morbidity were sacrificed. When mice were sacrificed, various organs were removed and stored at −80° C. At the end of the study (42 days of dosing), 3 and 5 mice treated with vehicle or Compound 2, respectively, were still alive. Quantitation of human tumor in the blood and marrow at death showed a statistical difference with the absolute percentage of human CD45+ in the bone marrow of 10.6% and 18.5% for the treated and untreated mice, respectively (FIGS. 9A-9B). The absolute percentage in the blood was 44.5% and 57.6% for treated and untreated mice, respectively.

Definitions

As used herein, each of the following terms has the meaning associated with it in this section.

Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, separation science, and organic chemistry are those well-known and commonly employed in the art.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

In one aspect, the terms "co-administered" and "co-administration" as relating to a subject refer to administering to the subject a compound of the disclosure or salt thereof along with a compound that may also treat any disease or disorder contemplated herein and/or with a compound that is useful in treating other medical conditions but which in themselves may cause or facilitate any disease or disorder contemplated herein. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "$ED_{50}$" refers to the effective dose of a formulation that produces 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the disclosure in a kit. The instructional material of the kit may, for example, be affixed to a container that contains the compound and/or composition of the disclosure or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "pharmaceutical composition" or "composition" refers to a mixture of at least one compound useful within the disclosure with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the disclosure, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the subject. Supplementary active compounds may also be incorporated into the compositions. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds," as used herein, is meant that a first molecule preferentially binds to a second molecule (e.g., a particular receptor or enzyme), but does not necessarily bind only to that second molecule.

As used herein, a "subject" may be a human or non-human mammal or a bird. Non-human mammals include, for example, livestock and pets, such as ovine, bovine, porcine, canine, feline and murine mammals. In certain embodiments, the subject is human.

The term "treat," "treating" or "treatment," as used herein, means reducing the frequency or severity with which symptoms of a disease or condition are experienced by a subject by virtue of administering an agent or compound to the subject.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl. In certain embodiments, the substituted alkyl is not substituted with a hydroxy group.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—CH$_3$, —CH═CH—CH$_2$—OH, —CH$_2$—CH═N—OCH$_3$, —CH═CH—N(CH$_3$)—CH$_3$, and —CH$_2$—CH═CH—CH$_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-(C$_1$-C$_3$)alkyl" means a functional group wherein a one to three carbon alkylene chain is attached to an aryl group, e.g., —CH$_2$CH$_2$-phenyl or —CH$_2$-phenyl (benzyl). Preferred is aryl-CH$_2$— and aryl-CH(CH$_3$)—. The term "substituted aryl-(C$_1$-C$_3$)alkyl" means an aryl-(C$_1$-C$_3$)alkyl functional group in which the aryl group is substituted. Preferred is substituted aryl (CH$_2$)—. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. Preferred is heteroaryl-(CH$_2$)—. The term "substituted heteroaryl-(C$_1$-C$_3$)alkyl" means a heteroaryl-(C$_1$-C$_3$)alkyl functional group in which the heteroaryl group is substituted. Preferred is substituted heteroaryl-(CH$_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of C$_{1-6}$ alkyl, —OH, C$_{1-6}$ alkoxy, halo, amino, acetamido and nitro. As used herein, where a substituent is an alkyl or alkoxy group, the carbon chain may be branched, straight or cyclic, with straight being preferred.

Throughout this disclosure, various aspects of the disclosure may be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

The disclosure contemplates any of the compounds recited herein, or a composition containing the same, or a salt, solvate, racemate (if applicable), enantiomer (if applicable), and/or tautomer (if applicable) thereof.

In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography. All possible stereochemical configurations of a given compound containing chiral center(s) are contemplated. All possible mixtures enriched with a particular enantiomer or diastereoisomer(s) are contemplated. All pure individual enantiomers or diastereoisomers are contemplated.

The methods and formulations described herein include the use of N-oxides (if appropriate), crystalline forms (also known as polymorphs), solvates, amorphous phases, and/or pharmaceutically acceptable salts of compounds having the structure of any compound of the disclosure, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the disclosure may exist as tautomers. "Tautomerization" is a form of isomerization involving the migration of a proton accompanied by changes in bond order, often the interchange of a single bond with an adjacent double bond. Where tautomerization is possible, (e.g., in solution), a chemical equilibrium of tautomers can be reached. One well known example of tautomerization is between a ketone and its corresponding enol. Heterocycles may form tautomers such as the interconversion of pyrrolidinone and hydroxypyrrole. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the disclosure is susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to 2H, 3H, $^{11}$H, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S.

In certain embodiments, isotopically labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Compounds of the disclosure can in certain embodiments form acids or bases. In certain embodiments, the disclosure contemplates acid addition salts. In other embodiments, the disclosure contemplates base addition salts. In yet other embodiments, the disclosure contemplates pharmaceutically acceptable acid addition salts. In yet other embodiments, the disclosure contemplates pharmaceutically acceptable base addition salts. Pharmaceutically acceptable salts refer to salts of those bases or acids that are not toxic or otherwise biologically undesirable.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the disclosure include, for example, metallic salts including alkali metal, alkaline earth metal and transition metal salts such as, for example, calcium, magnesium, potassium, sodium, lithium and copper, iron and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means.

Protective groups that are cleaved under totally disparate reaction conditions fulfill the requirement of differential removal.

Protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Combination Therapies

In certain embodiments, the compounds of the disclosure are useful in the methods of the disclosure in combination with at least one additional agent useful for treating, ameliorating, and/or preventing a disease or disorder contemplated herein. This additional agent can comprise compounds identified herein or compounds, e.g., commercially available compounds, known to treat, prevent, and/or reduce the symptoms of the disease or disorder contemplated herein.

In certain embodiments, the at least one additional agent is a genotoxic agent. In certain embodiments, the at least one additional agent is a chemotherapeutic agent. In some embodiments, the at least one additional agent is an anti-cancer agent. In certain embodiments, the at least one additional agent is radiation. In certain embodiments, the at least one additional agent is an immune checkpoint blockade inhibitor.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the compounds of the disclosure in prevention of the occurrence of tumor in the first place. The term "anti-tumor agent" or "anti-cancer agent" as used herein, refers to an agent that has an "anti-tumor effect."

The term "genotoxic agent" as used herein refers to a chemical compound, environmental agent, and/or external stimulation that is damaging to DNA. In certain embodiments, the genotoxic agent causes mutations in DNA. In certain embodiments, the genotoxic agent treats preferentially kills cancer over healthy cells of a patient. In certain embodiments, the genotoxic agent enhances the effectiveness of a compound described herein.

In certain embodiments, the anti-cancer agent is an immune checkpoint blockade inhibitor. Examples of immune checkpoint blockade inhibitors that can be utilized as described herein include, without limitation, an anti-PD1, PDL1, or CTLA4 immune checkpoint blockade inhibitor. In certain embodiments, the immune checkpoint blockade inhibitor is ipilimumab.

In certain embodiments, the chemotherapeutic is selected from the group consisting of cisplatin, carboplatin, 5-fluorouracil, cyclophosphamide, oncovin, vincristine, prednisone, or rituximab, mechlorethamine, cyclophosphamide, ifosfamide, melphalan, chlorambucil, carmustine, lomustine, semustine, thriethylenemelamine, triethylene thiophosphoramide, hexamethylmelamine altretamine, busulfan, triazines dacarbazine, methotrexate, trimetrexate, fluorodeoxyuridine, gemcitabine, cytosine arabinoside, 5-azacytidine, 2,2'-difluorodeoxycytidine, 6-mercaptopurine, azathioprine, 2'-deoxycoformycin, erythrohydroxynonyladenine, fludarabine phosphate, 2-chlorodeoxyadenosine, camptothecin, topotecan, irinotecan, paclitaxel, vinblastine, vincristine, vinorelbine, docetaxel, estramustine, estramustine phosphate, etoposide, teniposide, mitoxantrone, mitotane, and aminoglutethimide.

In certain embodiments, the at least one additional agent is selected from the group consisting of dabrafenib, vemurafenib, cobimetinib, trametinib, ipilimumab, nivolumab, and pembrolizumab.

A synergistic effect may be calculated, for example, using suitable methods such as, for example, the Sigmoid-$E_{max}$ equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Methods

The disclosure provides a method of treating, ameliorating, and/or preventing a CXCR5-expressing cancer in a subject in need thereof. In another aspect, the disclosure provides a method of treating, ameliorating, and/or preventing a CXCR5-mediated disease, disorder or condition in a subject in need thereof.

In certain embodiments, the cancer is a B-cell malignancy. In certain embodiments, the B-cell malignancy comprises at least one of diffuse large B-cell lymphoma (DLBCL), follicular lymphoma, marginal zone B-cell lymphoma (MZL) or mucosa-associated lymphatic tissue lymphoma (MALT), chronic lymphocytic leukemia (CLL), and mantle cell lymphoma (MCL). In certain embodiments, the follicular lymphoma comprises a T follicular helper derived lymphoma. In certain embodiments, the lymphoma comprises T cell lymphoma such as PTCL, angioimmunoblastic T cell lymphoma (AITL) and/or cutaneous T cell lymphoma (CTCL).

In certain embodiments, the method comprises administering to the subject a therapeutically effective amount of at least one compound of the disclosure. In other embodiments, the at least one compound of the disclosure is administered as a pharmaceutical composition comprising at least one pharmaceutically acceptable carrier. In other embodiments, the at least one compound of the disclosure is the only therapeutically effective agent administered to the subject. In yet other embodiments, the at least one compound of the disclosure is the only therapeutically effective agent administered to the subject in an amount that treats, ameliorates, and/or prevents the cancer in the subject.

In certain embodiments, the blood level of the compound is about 0.1 µM, 0.2 µM, 0.3 µM, 0.4 µM, 0.5 µM, 0.6 µM, 0.7 µM, 0.8 µM, 0.9 µM, 1 µM, 1.1 µM, 1.2 µM, 1.3 µM, 1.4 µM, 1.5 µM, 1.6 µM, 1.7 µM, 1.8 µM, 1.9 µM, 2.0 µM, 2.2 µM, 2.4 µM, 2.6 µM, 2.8 µM, 3 µM, 3.2 µM, 3.4 µM, 3.6 µM, 3.8 µM, 4 µM, 4.2 µM, 4.4 µM, 4.6 µM, 4.8 µM, 5 µM, 5.5 µM, 6 µM, 6.5 µM, 7 µM, 7.5 µM, 8 µM, 8.5 µM, 9 µM, 9.5 µM, or 10 µM.

In certain embodiments, the subject is a mammal. In other embodiments, the mammal is human.

In yet other embodiments, the at least one compound is administered by an administration route selected from the group consisting of inhalational, oral, rectal, vaginal, parenteral, intracranial, topical, transdermal, pulmonary, intranasal, buccal, ophthalmic, intrathecal, and intravenous.

In certain embodiments, the subject is further administered at least one additional agent that treats the disease and/or disorder. In other embodiments, the compound and the at least one additional agent are co-administered. In yet other embodiments, the compound and the at least one additional agent are co-formulated.

Kits

The disclosure includes a kit comprising at least one compound contemplated herein, optionally an applicator, and instructional material for use thereof.

The instructional material included in the kit comprises instructions for preventing, ameliorating, and/or treating a B-cell and/or T-cell malignancy in a subject. The instructional material recites the amount of, and frequency with which, the compound should be administered to the mammal. In certain embodiments, the kit further comprises at least one additional agent=for preventing, ameliorating, and/ or treating a B-cell and/or T-cell malignancy in a subject. In other embodiments, the kit further comprises at least one additional anti-cancer agent.

Administration/Dosage/Formulations

The disclosure also encompasses pharmaceutical compositions and methods of their use. These pharmaceutical compositions may comprise an active ingredient (which can be one or more compounds of the disclosure, or pharmaceutically acceptable salts thereof) optionally in combination with one or more pharmaceutically acceptable agents. The compositions set forth herein can be used alone or in combination with additional compounds to produce additive, complementary, or synergistic effects.

The regimen of administration may affect what constitutes an effective amount. The therapeutic formulations may be administered to the subject either prior to or after the onset of a disease or disorder contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, preferably a mammal, more preferably a human, may be carried out using known procedures, at dosages and for periods of time effective to treat a disease or disorder contemplated herein. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated herein. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect, and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated herein.

In certain embodiments, the compositions of the disclosure are formulated using one or more pharmaceutically acceptable excipients or carriers. In certain embodiments, the pharmaceutical compositions of the disclosure comprise a therapeutically effective amount of a compound of the disclosure and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

In certain embodiments, the compositions of the disclosure are administered to the patient in dosages that range from one to five times per day or more. In other embodiments, the compositions of the disclosure are administered to the patient in range of dosages that include, but are not limited to, once every day, every two, days, every three days to once a week, and once every two weeks. It is readily apparent to one skilled in the art that the frequency of administration of the various combination compositions of the disclosure varies from individual to individual depending on many factors including, but not limited to, age, disease or disorder to be treated, gender, overall health, and other factors. Thus, the disclosure should not be construed to be limited to any particular dosage regime and the precise dosage and composition to be administered to any patient is determined by the attending physical taking all other factors about the patient into account.

Compounds of the disclosure for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In certain embodiments, the dose of a compound of the disclosure is from about 1 mg and about 2,500 mg. In other embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in other embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of a disease or disorder contemplated herein.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the disclosure include oral, nasal, rectal, intravaginal, parenteral, buccal, sublingual or topical. The compounds for use in the disclosure may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the disclosure may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present disclosure also includes a multi-layer tablet comprising a layer providing for the delayed release of one or more compounds of the disclosure, and a further layer providing for the immediate release of a medication for treatment of diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the disclosure may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 20030147952; 20030104062; 20030104053; 20030044466; 20030039688; and 20020051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the disclosure may be administered in the form of microparticles, for example, by injection or in the form of wafers or discs by implantation.

In certain embodiments, the compounds of the disclosure are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present disclosure depends on the age, sex and weight of the patient, the current medical condition of the patient and the progression of a disease or disorder contemplated herein in the patient being treated. The skilled artisan is able to determine appropriate dosages depending on these and other factors.

A suitable dose of a compound of the present disclosure may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the disclosure is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the cancer, to a level at which the improved disease is retained. In certain embodiments, patients require intermittent treatment on a long-term basis upon any recurrence of symptoms and/or tumors.

The compounds for use in the method of the disclosure may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents are considered to be within the scope of this disclosure and covered by the claims appended hereto. For example, it should be understood, that modifications in assay conditions and/or reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

Experimental Examples

The disclosure is now described with reference to the following Examples. These Examples are provided for the purpose of illustration only and the disclosure should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, point out specific embodiments of the present disclosure, and are not to be construed as limiting in any way the remainder of the disclosure.

Materials and Methods:

Calcium Assay

The calcium assay allows homogeneous measurement of intracellular calcium changes caused by activation of G-protein coupled receptors or calcium channels. The assay involves only one dye addition step and does not require washing, allowing easy implementation in a high throughput environment.

Cell Preparation:

Cell number needs to be optimized for each assay. Optimal assay conditions require a confluent monolayer of cells prior to the assay.

For adherent cells, plate 50K to 70K cells/well for a 96 well plate and 12K to 20K cells/well for a 384 well plate the day before the experiment. Add 100 µl/well of cell suspension to 96-well plates or 25 µl/well to 384-well plates, allow cells to attach and grow overnight for 16 to 24 hours in cell culture incubators. Prior to dye loading the plate, examine the cells for confluency and overall health.

For non-adherent cells, dispense 100 µl/well of cells in culture medium to 96-well or 25 µl/well to 384-well poly-D Lysine or other ECM coated plates a couple of hours before the experiment. Allow cells to settle and attach to the bottom of the plates at room temperature.

Centrifuge briefly with brake off prior to the experiment.
Preparation of 1× Dye-Loading Solution
1. Remove a vial of Calcium Indicator from −20° C., and allow to sit at room temperature for 5 minutes to warm up. Add 100 μl 100% DMSO, reconstitute the pellet by pipetting up and down several times.
2. To prepare 1× Signal Enhancer, transfer 10 ml of 10×Signal Enhancer to 90 ml of 1× Calcium Assay buffer, mix well.
3. To prepare 1×Dye-loading Solution for one cell plate, pipette 10 ml of 1× Signal Enhancer to a separate tube, add 10 μl of Calcium Indicator to 10 ml of 1× Signal Enhancer, mix by inverting the tube several times.
4. Aliquot the unused Calcium Indicator to several microfuge tubes, seal tightly and store at −20° C. protected from light. 1× Signal Enhancer could be stored at room temperature.
Dye Loading:
1. Remove cell plates from incubator and add an equal volume of 1× Dye-loading Solution to each well (e.g. 100 μl to 100 μl culture medium/well for 96-well plates, or 25 μl to 25 μl culture medium/well for 384-well plates). 2. Incubate cell plates with dye for 1 hour in cell culture incubator.
Calcium Flux Assay:
Place the cell plates on a FLIPR, FlexStation or FDSS, and perform calcium flux assay as described in instrumentation manuals.
For assays performed on a FlexStation, use the following wavelength parameters: Excitation: 485 nm; Emission: 525 nm; AutoCutoff: on (515 nm).
For assays performed on a FLIPR and an FDSS, use the standard filters for calcium assays.
In Vivo Efficacy:
Implantation:
PDX was implanted into immunocompromised NSG mice.
Engraftment:
Starting at around 21 days after implantation, animals are examined for engraftment every 1-2 weeks. Engraftment is determined by measuring human CD45+ cells in blood (flow cytometry).
Dosing:
After engraftment is observed, animals are dosed by oral gavage every 10-14 hours with vehicle (untreated groups) or with compound YU241279 at 40 mg/kg (treated groups).
Analysis:
Animals are evaluated for general health daily and weighed twice per week; circulating human CD45+ cells are measured on days 14 and 28 after treatment initiation to evaluate tumor progression. Based on day 28 analysis, treatment may be extended (the decision to extend the dosing is based on the health status of the vehicle group: CD45 (<50%), lack of morbidity by day 28); Readouts at conclusion of the study include spleen weight, survival, and flow cytometry assessment for human CD45+ cells in blood and bone marrow.

The disclosures of each and every patent, patent application, and publication cited herein are hereby incorporated herein by reference in their entirety.

While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A method of treating, or ameliorating a CXCR5-expressing cancer in a subject, wherein the method comprises administering to the subject a therapeutically effective amount of a compound selected from:
2-(3-methyl-2-(2-methylprop-1-en-1-yl)benzamido)-2,3-dihydro-1H-indene-2-carboxylic acid,
2-(2-isobutyl-3-methylbenzamido)-2,3-dihydro-1H-indene-2-carboxylic acid,
or a salt, solvate, or tautomer thereof, or any mixtures thereof, wherein the cancer is a B-cell malignancy.

2. The method of claim 1, wherein the B-cell malignancy comprises at least one of diffuse large B-cell lymphoma (DLBCL), follicular lymphoma, marginal zone B-cell lymphoma (MZL) or mucosa-associated lymphatic tissue lymphoma (MALT), chronic lymphocytic leukemia (CLL), and mantle cell lymphoma (MCL).

3. The method of claim 2, wherein the follicular lymphoma comprises a peripheral T-cell lymphoma (PTCL).

4. The method of claim 3, wherein the PTCL comprises at least one of T follicular helper derived lymphoma, angioimmunoblastic T cell lymphoma (AITL), and/or cutaneous T cell lymphoma (CTCL).

5. The method of claim 4, wherein the CTCL comprises mycosis fungoides and/or the Sezary Syndrome.

6. The method of claim 1, wherein the compound is administered as a pharmaceutical composition comprising at least one pharmaceutically acceptable carrier.

7. The method of claim 1, wherein the compound is the only therapeutically effective agent administered to the subject.

8. The method of claim 1, wherein the compound is the only therapeutically effective agent administered to the subject in an amount that treats, or ameliorates the cancer in the subject.

9. The method of claim 1, wherein the blood level of the compound in the subject is about 1 μM.

10. The method of claim 1, wherein the subject is a mammal.

11. The method of claim 1, wherein the subject is human.

12. The method of claim 1, wherein the compound is administered by an administration route selected from the group consisting of inhalational, oral, rectal, vaginal, parenteral, intracranial, topical, transdermal, pulmonary, intranasal, buccal, ophthalmic, intrathecal, and intravenous.

13. The method of claim 1, wherein the subject is further administered at least one additional agent that treats, or ameliorates, and/or prevents the cancer.

14. The method of claim 1, wherein the compound and the at least one additional agent are co-administered.

15. The method of claim 1, wherein the compound and the at least one additional agent are co-formulated.

* * * * *